(12) United States Patent
Zimmermann et al.

(10) Patent No.: US 9,926,551 B2
(45) Date of Patent: Mar. 27, 2018

(54) ENCAPSULATING DEVICE AND ENCAPSULATING METHOD FOR ENCAPSULATING A SAMPLE IN A POLYMER CAPSULE

(71) Applicant: Fraunhofer-Gesellschaft zur Foerderung der angewandten Forschung e.V., Munich (DE)

(72) Inventors: Heiko Zimmermann, Waldbrunn (DE); Julia Neubauer, St. Ingbert (DE)

(73) Assignee: Fraunhofer-Gesellschaft zur Foerderung der angewandten Forschung e. V., Munich (DE)

( * ) Notice: Subject to any disclaimer, the term of this patent is extended or adjusted under 35 U.S.C. 154(b) by 31 days.

(21) Appl. No.: 14/902,072

(22) PCT Filed: Jun. 27, 2014

(86) PCT No.: PCT/EP2014/001776
§ 371 (c)(1),
(2) Date: Dec. 30, 2015

(87) PCT Pub. No.: WO2015/010763
PCT Pub. Date: Jan. 29, 2015

(65) Prior Publication Data
US 2016/0201050 A1  Jul. 14, 2016

(30) Foreign Application Priority Data
Jul. 26, 2013  (DE) .................. 10 2013 012 467

(51) Int. Cl.
C12N 11/04  (2006.01)
C12M 1/12  (2006.01)
(Continued)

(52) U.S. Cl.
CPC ............... *C12N 11/04* (2013.01); *B01J 13/14* (2013.01); *B01J 13/206* (2013.01); *C12M 25/01* (2013.01);
(Continued)

(58) Field of Classification Search
CPC .................. B01J 13/14; B29B 9/12
(Continued)

(56) References Cited

U.S. PATENT DOCUMENTS 3,639,306 A  2/1972  Sternberg et al.
5,882,680 A  3/1999  Suzuki et al.
(Continued)

FOREIGN PATENT DOCUMENTS

| DE | 1939066 A1 | 2/1970 |
| DE | 10203629 A1 | 7/2003 |
| DE | 69628394 T2 | 3/2004 |

OTHER PUBLICATIONS

International Search Report for PCT/EP2014/001776 dated Oct. 14, 2014.
(Continued)

*Primary Examiner* — Joseph S Del Sole
*Assistant Examiner* — Thu Khanh T. Nguyen
(74) *Attorney, Agent, or Firm* — Caesar Rivise, PC (57) ABSTRACT

The invention relates to an encapsulating device (100), which is designed to encapsulate a sample (1, 2) in a polymer capsule, comprising a drop generator (10), which is designed to provide a drop (3) of a suspension, which drop contains the sample (1), and a cross-linking device (20), which is designed to polymerize the drop (3), wherein the drop generator (10) has a retaining device (11), which is designed to accommodate the drop (3) in a hanging state, and the cross-linking device (20) is designed to feed a polymerization substance to the hanging drop (3) on the
(Continued)

retaining device (11) and to form the polymer capsule. The invention further relates to a method for encapsulating a sample (1, 2) in a polymer capsule.

18 Claims, 4 Drawing Sheets

(51) Int. Cl.
  *C12N 11/10* (2006.01)
  *B01J 13/14* (2006.01)
  *B01J 13/20* (2006.01)
  *A61K 35/12* (2015.01)

(52) U.S. Cl.
  CPC ........ *C12N 11/10* (2013.01); *A61K 2035/128* (2013.01)

(58) Field of Classification Search
  USPC ........................................ 425/7–10
  See application file for complete search history.

(56) References Cited

U.S. PATENT DOCUMENTS

| | | |
|---|---|---|
| 8,563,082 B2 | 10/2013 | Zimmermann et al. |
| 2005/0158395 A1 | 7/2005 | Zimmermann et al. |
| 2005/0282264 A1 | 12/2005 | Yu et al. |
| 2009/0297595 A1 | 12/2009 | Zimmerman et al. |
| 2010/0219545 A1* | 9/2010 | Park ........................ A61J 3/07 425/10 |
| 2011/0229580 A1* | 9/2011 | Srivastava ........... A61K 9/1652 264/4 |

OTHER PUBLICATIONS

Chuah et al.: "Preparation of uniformly sized alginate microspheres using the novel combined methods of microchannel emulsification and external gelation", Colloids and Surfaces A: Physicochemical and Engineering Aspects, Elsevier, Amsterdam, NL, Bd. 351, Nr. 1-3, Nov. 5, 2009 (Nov. 5, 2009), pp. 9-17.

Kelm et al.: "Method for generation of homogeneous multicellular tumor spheroids applicable to a wide variety of cell types", Biotechnology and Bioengineering, Bd. 83, Nr. 2, Jul. 20, 2003 (Jul. 20, 2003), pp. 173-180.

Zimmermann et al. "Physical and biological properties of barium cross-linked alginate membranes." Biomaterials 28.7 (2007): 1327-1345.

Zimmermann et al. "A Novel Class of Amitogenic Alginate Microcapsules for Long-Term Immunoisolated Transplantation." Annals of the New York Academy of Sciences 944.1 (2001): 199-215.

\* cited by examiner

ENCAPSULATING DEVICE AND ENCAPSULATING METHOD FOR ENCAPSULATING A SAMPLE IN A POLYMER CAPSULE

BACKGROUND OF THE INVENTION

The invention relates to an encapsulating device, which is arranged to encapsulate a sample, in particular comprising at least one biological cell, in a polymer capsule, for example in an alginate capsule. Furthermore, the invention relates to a method for encapsulating a sample in a polymer capsule, in particular using the said encapsulating device. Application of the invention are available, in particular, in the encapsulation of biologically active samples, e.g. biological cells such as, for example, pluripotent stem cells or primary-tissue cells, in biocompatible polymers such as, for example, alginate.

It is generally known to immobilize biologically active substances such as, for example, enzymes, proteins, biological cells, cell components or cell groups, for applications in chemical, biochemical or medical procedures. The immobilization may include completely covering (encapsulating) the substance in a matrix material (encapsulating substance). For example, for applications in regenerative medicine, it is known to embed cells, tissue or micro-organs, as transplants, in a biocompatible encapsulating substance. The encapsulation offers the possibility, advantageously, of protecting the transplants against an immune response of a recipient, and against mechanical stress, while, at the same time, ensuring that the supply of nutrient to the transplant is maintained.

Frequently, encapsulation in three-dimensional, for example spherical, capsules is of interest, since, for biological cells, the three-dimensional environment is similar to a physiological environment, so that the cells keep better than in a layer-type encapsulation, for example on the surface of a substrate. For example, it is known that only in a three-dimensional environment do chondrocytes produce the collagen typical to the formation of cartilage, this being one reason for the delayed healing of cartilage defects.

Frequently used as an encapsulating substance is the polymer alginate. Alginate, besides cellulose, is a principal structural component of the cell walls of marine brown algae (phaeophyceae). Alginate is an acid polysaccharide, composed of 1-4-linked $\alpha$-L-guluronic acid and $\beta$-D-mannuronic acid chains. Homopolymer regions (MM blocks or GG blocks) and heteropolymer regions (MG blocks) are formed. The carboxyl groups of the acid chains can be cross-linked by bivalent cations (for example, $Ca^{2+}$, $Ba^{2+}$, $Fe^{2+}$). In the cross-linked state, alginate forms a hydrogel, which has proved to be advantageous for encapsulating biologically active substances. The viscosity of the cross-linked alginate increases as the concentration of cations increases, and alginate cross-linked with calcium or barium is stable at physiological temperatures.

Various methods are known for encapsulating, for example, biological cells in alginate. For example, it is known to generate drops of a suspension of biological cells in an alginate solution by means of compressed air, and to move them into a bath of a polymerization substance having bivalent cations, where cross-linking of the alginate chains occurs (see U. Zimmermann et al. in "Ann. N.Y. Acad. Sci.", volume 944, 2001, pp. 199-215). In the case of a further known method, falling drops of a cell-alginate suspension are bombarded with crystallites containing bivalent cations, thereby promoting internal cross-linking of the drops (see H. Zimmermann et al. in "Biomaterials" volume 28, 2007, pp. 1327-1345).

The conventional methods for encapsulating cells have several disadvantages. Firstly, the conventional techniques are distinguished by a high consumption of cells and alginate solution. In the generation of the falling suspension drops, the desired cell, or the desired number of cells, is not contained in each drop. The reproducibility of the encapsulation is dependent on numerous procedure conditions, and particularly on the capabilities of the person performing the encapsulation. Finally, there are limitations in combining the conventional encapsulation methods with complex processes in the cultivation (propagation, growth and/or differentiation) of biological cells. The latter is of importance, in particular, in the handling of therapeutically relevant cells such as, for example, stem cells. For the encapsulation of stem cells, in particular, there is an interest in three-dimensional embedding, since this three-dimensional embedding can be expected to have advantages for the proliferation and development of the cells.

A further known application of encapsulation in biocompatible polymers, for example alginate, is that of cryoconservation. The protective covering of the cells can reduce mechanical stress caused by any extra-cellular ice crystal formation and, in the case of cryoconservation of cell aggregates, cell-to-cell contacts can be protected.

Conventional immobilization techniques are not limited to the encapsulation of biologically active substances in alginate. Likewise, in other tasks of encapsulating substances in polymers, such as, for example, insulin in chitosan, there is an interest in embedding in three-dimensional, for example spherical or drop-shaped, capsules.

Furthermore, it is known to cultivate cells in hanging droplets, e.g. for the defined formation and cultivation of three-dimensional, multicellular aggregates. Hitherto, the conventional techniques have been limited exclusively to the cultivation of the cells in the hanging droplets.

It is the objective of the invention to provide an improved encapsulation device, with which disadvantages of conventional techniques are avoided. The encapsulation device is intended, in particular, to enable encapsulation with improved yield, increased reproducibility and/or reduced stress for the encapsulated sample. Furthermore, specifically, there is interest in an improved encapsulation device that is suitable for encapsulating samples comprising at least one biological cell, and that simplifies integration into processes for handling biological cells. It is a further objective of the invention to provide an improved method for encapsulating a sample in a polymer capsule, with which disadvantages of conventional methods are avoided. The encapsulation method is to be distinguished by an increased yield, improved reproducibility and/or reduced stress on the encapsulated samples.

These objectives are achieved by an encapsulation device and/or an encapsulation method having the features of the invention.

SUMMARY OF THE INVENTION

According to a first general aspect of the invention, the said objective is achieved by an encapsulation device that is arranged to encapsulate a sample in a polymer capsule, and that comprises a drop generator and a cross-linking device. The drop generator is arranged to form a drop (droplet) of a suspension that contains the sample to be encapsulated. According to the invention, the drop generator has a holding device, which is arranged to receive the drop in a hanging state. The cross-linking device is arranged to polymerize the drop. According to the invention, the cross-linking device is arranged to supply a polymerization substance to the hanging drop on the holding device and to form the polymer capsule (polymerized drop).

According to a second aspect of the invention, the said object is achieved by a method for encapsulating a sample in a polymer capsule, in which a drop of a suspension that contains the sample to be encapsulated is provided in a hanging state and is polymerized, as a hanging drop, by means of a polymerization substance, such that the polymer capsule is formed. Preferably, the method according to the invention is performed by means of the encapsulation device according to the above first aspect of the invention.

The polymerization of the suspension drop is effected when the latter has been positioned, in the hanging state, on the holding device. The holding device constitutes, in general, a receptacle for the hanging suspension drop. The hanging state of the suspension drop means that a top side of the suspension drop, i.e. a side that faces upwards in respect of the vertical direction (in opposition to gravity) adheres to the holding device. The hanging drop is motionless on the holding device. The underside of the hanging drop, i.e. the side that faces downwards in respect of the vertical direction (in the direction of gravity) may be entirely free (freely hanging drop) or supported by an additional holding element (supported hanging drop), the shape of the hanging drop being in each case determined by the surface tension of the suspension acting in combination with the holding device and, if applicable, the holding element.

Unlike the conventional techniques, the provision of the hanging drop allows the suspension drop to be provided in a stationary state. The drop has a fixed position relative to the cross-linking device. This makes it possible to ensure, prior to polymerization, that a drop contains the sample to be encapsulated. The polymerization of drops that do not contain a sample, for instance, is precluded. The shape of the drop is determined in a reproducible manner by properties of the suspension and of the holding device (if applicable, with the holding element). This enables the conditions for the supplying of the polymerization substance to the hanging drop to be set with increased reproducibility, this having an advantageous effect upon the reproducibility of the encapsulation. Furthermore, the gentle placing of the sample in the hanging drop avoids unwanted shear forces, such as may occur in the conventional formation of suspension drops, for example by means of compressed air.

A further advantage, which pertains particularly in the encapsulation of biological samples, consists in that the polymerization can be combined with the cultivation (propagation, growth and/or differentiation) of biological cells, in particular with cultivation in hanging drops (hanging droplets). The encapsulating device may be configured as part of a cultivation device for biological cells, in which the cells are cultivated and, if applicable, encapsulated, in hanging drops.

The encapsulation device may be designed, advantageously, to encapsulate a single sample in a single drop. In this case, the holding device constitutes a receptacle for one single drop. Alternatively, the encapsulation device may be arranged to simultaneously or successively encapsulate a multiplicity of samples in a multiplicity of drops. In this case, the holding device constitutes a receptacle for a plurality of drops in the hanging state. If, in the description of the present invention, reference is made to the encapsulation of a sample in a drop, this is intended to include the corresponding encapsulation of a multiplicity of samples in a multiplicity of drops.

Advantageously, there are various possibilities for configuring the holding device to receive the hanging drop. According to a first variant, the holding device comprises a holding plate, having an exposed underside that is arranged to receive the hanging drop. The holding plate, which may be made, for example, of transparent material such as, for example, glass or plastic, has the advantage that the hanging drop is protected, on its top side, against unwanted influences. For the purpose of locating the hanging drop, the exposed underside of the holding plate may be provided at a particular position with a hydrophilic surface.

According to a second variant of the invention, the holding device may have a hole plate, which has a hole for receiving the hanging drop or—for the encapsulation of a multiplicity of samples—a multiplicity of holes, each respectively for receiving a hanging drop. The suspension drop is held in the hole under the action of the surface tension. The use of the hole plate has the advantage that there is access to the hanging drop on both sides of the hole plate, for example for the feeding of substances and/or for feeding the sample.

According to a third variant of the invention, the holding device may comprise a mesh plate (lattice plate) that is arranged to receive the hanging drop. The mesh plate is constituted by a mesh structure having a multiplicity of openings, a group of openings in each case constituting a receptacle for the hanging drop. Since the drop, in the hanging state, is in contact with a plurality of mesh rods, the mesh plate may be distinguished in that, in comparison with the holding plate, for example, it has a greater retaining force.

Finally, the holding device according to a further variant may be one-dimensional in form, in the shape of a holding rod that is arranged to receive the hanging drop, preferably to receive a row of hanging drops.

The said variants may be provided singly or in combinations. For example, the holding device may have, in a first portion, a closed holding plate for hanging drops and, with a second portion, have a non-closed plate such as, for example, a hole plate or a mesh plate. Furthermore, the holding device may be provided with the additional, supporting holding element on the underside of, for example, the holding plate, hole plate, mesh plate or holding rod.

According to a preferred embodiment of the invention, the drop generator has a feed device, by means of which the suspension can be routed to the holding device. The feed device is arranged to form the hanging drop on the holding device. Advantageously, the feed device simplifies the operation of the drop generator. Particularly preferred is an embodiment of the invention in which the feed device comprises a pipetting device (first pipetting device), which is arranged to place the hanging drop on the holding device. Advantageously, the use of the first pipetting device simplifies combining the encapsulation with further process steps of the handling of biological cells. Unlike the conventional techniques, it is possible to dispense with the use of additional appliances such as, for example, a compressed-air generator for generating drops.

The cross-linking device of the encapsulation device according to the invention is arranged, in general, to bring the polymerization substance into contact with the suspension in the hanging state. Advantageously, there are various possibilities for delivering the polymerization substance to the hanging drop. According to a first variant, the cross-linking device comprises a pipetting device (second pipetting device), by means of which the polymerization substance can be introduced, in the fluid state, into the hanging drop. For example, the holding device may be provided with the above-mentioned first pipetting device for placing the hanging drop, and with the second pipetting device for supplying the polymerization substance into the hanging drop. The use of the second pipetting device may have advantages in respect of gentle supplying of the polymerization substance and/or supplying of a defined volume of the polymerization substance.

According to a second variant, the cross-linking device may have a particle shooting device, which is arranged to inject the polymerization substance, in the form of solid particles (crystallites) into the hanging drop. In this case, advantages may be gained from spatially separating the cross-linking device from the hanging drop, and from avoiding unintentional contamination of the hanging drop with extraneous substances.

According to a further variant, the polymerization substance may be provided in a bowl. The bowl is positioned beneath the holding device, and the holding device and the bowl are movable relative to each other, such that the hanging drop can be immersed in the polymerization substance in the bowl. This configuration of the invention may have advantages for the simultaneous polymerization of a plurality of drops, i.e. for simultaneous encapsulation of a plurality of samples.

The inventors have found that the drop, even after polymerization, i.e. the polymer capsule, can adhere to the holding device. It is conducive to the adherence of the polymer capsule if, in particular, a hole plate or a mesh plate is used as a holding device. Advantageously, the polymer capsule, on the holding device, can be subjected to further processing steps, in particular to covering with a fluid covering substance. For this purpose, according to a further preferred embodiment of the encapsulation device according to the invention, the holding device is additionally provided with a covering device, which is arranged to cover the polymer capsule with the covering substance.

Preferably, the covering device comprises at least one fluid line for supplying the covering substance to the polymer capsule, the covering line being fixedly connected to the holding device. Alternatively, a third pipetting device may be provided for supplying the covering substance.

According to a further advantageous embodiment of the invention, the encapsulation device is provided with a measuring device. The measuring device, based, for example, on an optical or electrical measurement, is provided for examining the hanging drop and/or the polymer capsule. Advantageously, the measuring device makes it possible to check, prior to the polymerization of the drop, whether the desired sample is present in the latter, whether the hanging drop has the desired shape and/or whether the polymerization has resulted in an adequate encapsulation of the sample.

Further advantages for the use of the encapsulation device are obtained if the latter is provided, according to a further embodiment of the invention, with a separating device, by means of which the polymer capsule can be parted off from the holding device. The separating device, which comprises, for example, a scraper blade on the underside of the holding device, allows the polymer capsule to be transferred into a collecting vessel for preparation for further use, for example for transplantation purposes or for the cryoconservation of the encapsulated sample.

The invention may be realized with a multiplicity of polymers for encapsulating samples. The sample comprises, in general, a synthetic and/or natural material. Preferably, the sample comprises biologically active material, in particular at least one biological cell, cell components, macromolecules that are active in cells, such as, for example, enzymes, proteins or nucleic acids, cell groups, cell tissue or organs composed of cell groups. Available polymers may be used as an encapsulation substance, such as, for example, alginate, gelatin, agarose, chitosan, or silicone.

The suspension in which the sample is contained may comprise a polymer solution, in particular an alginate solution, while the polymerization substance contains a cross-linking means, in particular cross-linking ions for cross-linking alginate. In this case, the hanging drop is formed by the polymer solution, in particular alginate solution, in which the sample is suspended. Alternatively, the suspension may contain the cross-linking means, in particular cross-linking ions for cross-linking alginate, while the polymerization substance comprises an alginate solution, which is polymerized after being fed to the hanging drop.

In general, the encapsulation, according to the invention, of samples, in particular biological cells, has the following advantages. The encapsulation of cells can be performed in a defined and reproducible manner, in that the number of cells or cell aggregates per hanging drop is controlled. The sedimentation of the sample in the hanging drop can be exploited for the purpose of selectively positioning the sample in the encapsulated state. Alternatively, a uniform distribution of the sample, in particular of the cells or cell aggregates, in the hanging drop can be ensured by resuspending the cell suspension immediately before cross-linking. It is thus also possible, if necessary—by integration of appropriate pipetting steps—to avoid the sample being positioned in the outer periphery.

In the encapsulation process, hanging drops are positioned exactly and parted-off. Following cross-linking, the polymer capsules preferably remain adhering to the underside of the plate, such that they can be parted-off in a selective and specific manner for a further use. Unlike conventional methods, in which an unknown number of alginate capsules are obtained, which can then scarcely be separated, owing to their small size, the encapsulation according to the invention makes it possible to achieve an exact number of polymer capsules, of a defined size, which results, for example, from the previously pipetted drop volume.

The formation of capsules without samples is precluded, and subsequent checking or separating of non-charged particles is not necessary. The polymer capsules produced according to the invention have a defined size. In the case of encapsulation of a plurality of samples, the capsules are virtually identical in size. Finally, the invention makes it possible to encapsulate cells during or after cultivation in the hanging drop, and there is no need, for instance, for enzymatic removal of growth surfaces. Stress on the cells is avoided.

Moreover, a further important advantage of the encapsulation in hanging drops is that it can be easily integrated into existing cell culture sequences, since the hanging drop was originally proposed and developed for cultivating and differentiating cells. Whereas, prior to the invention, this method was limited to applications that do not require cells to adhere to surfaces, since only the formation of three-dimensional cell aggregates is possible inside the drop, the integration of microcarriers—mostly spherical carrier particles having a diameter in the range of from 50 μm to 500 μm, on the surface of which the cells can adhere—means that virtually all cell culture processes can be transferred into the hanging drop. For examples, cells can be first cultivated either in suspension or together with microcarriers in the hanging drop. For this purpose, the drops of the corresponding cell suspension are placed, for example, at the drop plate of the holding device, either manually or by means of a pipetting robot. Automatic or manual cultivation, differentiation or high-throughput screening for active substances, in the context of medicament developments, can then be performed. The cellular end product that is produced in this case, or also any intermediate products, can be encapsulated in alginate at any time, in that the culture medium or differentiation medium is replaced by the alginate solution and cross-linked according to the invention.

BRIEF DESCRIPTION OF SEVERAL VIEWS OF THE DRAWINGS

Further details and advantages of the invention are described in the following, with reference to the appended drawings. There are shown in.

DETAILED DESCRIPTION OF PREFERRED EMBODIMENTS

Embodiments of the invention are described in the following, in particular, with reference to the design of the encapsulation device and the polymerization of drops in the freely hanging state. In this, reference is made, exemplarily, to the encapsulation of biological cells in alginate capsules. It is emphasized that the invention is not limited to this application, but is correspondingly possible with other samples, in particular biologically active substances and/or other materials, and/or other polymers and/or with drops that hang in a supported manner. Details of the selection of the polymer material and of the cross-linking means, in particular the setting of concentrations or the selection of bivalent cations, and details of the handling of biological cells, are not described, since these are known per se from conventional techniques.

The invention is described, in particular, in reference to the drop generator with the holding device and the cross-linking device, and their mutual interaction. The encapsulation device may have further components such as, for example, fluid reservoirs, pumps, temperature control devices, moistening devices and the like. The encapsulation device may comprise, in particular, an autonomous appliance for laboratory or industrial applications for the production of encapsulated samples in polymer capsules. Alternatively, the encapsulation device may be part of a cultivation appliance for biological cells that is configured, in particular, for cultivating cells in hanging drops. In this case, the drop generator, with the holding device, simultaneously constitutes a substrate for the cultivation of cells in hanging drops.

The embodiments of the invention are described in the following with exemplary reference to the provision and polymerization of single hanging drops. It is emphasized that the invention can be implemented, correspondingly, with groups of hanging drops. For the mass-production of samples in polymer capsules, large numbers of hanging drops, for example 100, 1000 or more, can be provided simultaneously and polymerized at the same time or in succession.

Figure 1:
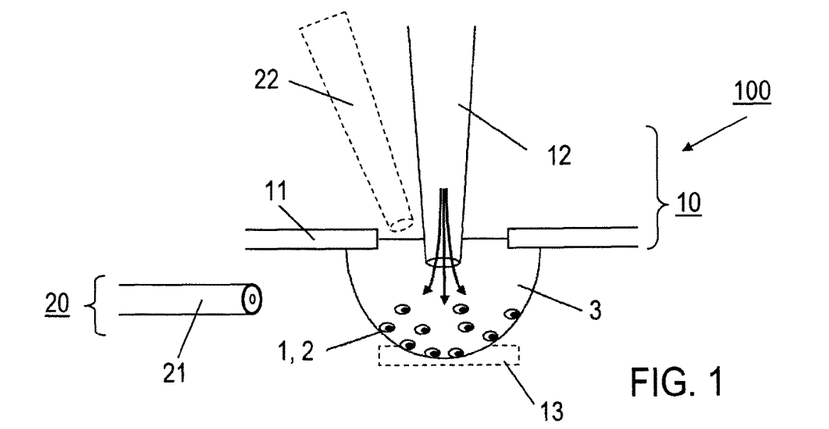
FIG. 1: the formation of a hanging drop according to an embodiment of the invention.

FIG. 1 illustrates features of preferred embodiments of the encapsulation device 100 according to the invention (shown in part), having a drop generator 10 and a cross-linking device 20. The drop generator 10 comprises a holding device 11 in the form of a hole plate. Furthermore, in the case of the embodiment represented, the holding device 11 is provided with a feed device 12, comprising a first pipetting device. The feed device 12 may be movable in relation to the holding device 11 or fixedly connected to the latter. The hole plate is a flat, solid plate having at least one hole, which plate extends in the horizontal direction in the encapsulation device 100. The thickness of the plate is, for example, 3 mm, and the diameter of the at least one hole is, for example, 100 µm to 5 mm. The hole plate is, for example, a drop plate, which is commercially available for the cultivation of hanging drops.

An optionally provided holding element 13 (indicated by a broken line) is illustrated in FIG. 1. The holding element 13 may be provided in the form of, for example, a plate or bar for supporting the drop (supported hanging drop).

The cross-linking device 20 comprises, for example, a particle shooting device 21 and/or a second pipetting device 22 (indicated by a broken line). The type of the cross-linking device 20 is selected in dependence on the specific application of the invention. For example, injection of solid particles of the polymerization substance by means of the particle shooting device 21 is preferred if a rapid polymerization of the total volume of the hanging drop is desired. On the other hand, the use of the second pipetting device 22 may have advantages if a slow polymerization from one side of the hanging drop is preferred. The two types of cross-linking devices may be combined. Furthermore, cross-linking in a bowl may be provided (see below, FIG. 3).

For the encapsulation of a sample comprising biological cells 2 (for examples, see below), a hanging drop 3 is first placed on the hole plate of the holding device 11 by means of the feed device 12. The feed device 12 may be actuated manually or by means of a drive device (pipetting robot) controlled by a processor. For example, a drop having a diameter of 4 mm, having 1000 suspended cells, is formed. The feed device 12 may be used, furthermore, to add further substances such as, for example, nutrients or synthetic particles (so-called "microcarriers") to the drop 3.

Figure 2:
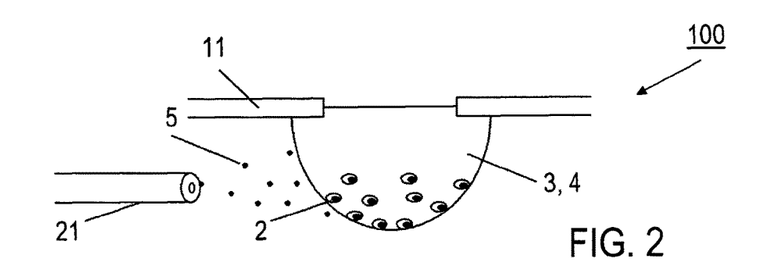
FIG. 2: a first variant of the polymerization of the hanging drop according to FIG. 1.

Following formation of the drop 3 in the hanging state, the alginate solution is polymerized by supplying of a polymerization substance 5 (FIG. 2). The polymerization substance 5 comprises crystallites that have bivalent cations. The particle shooting device 21 contains, for example, a crystallite reservoir (not represented), by means of which crystallites are injected through a guide tube into the hanging drop 3, by means of a compressed-air source (not represented).

Figure 3:
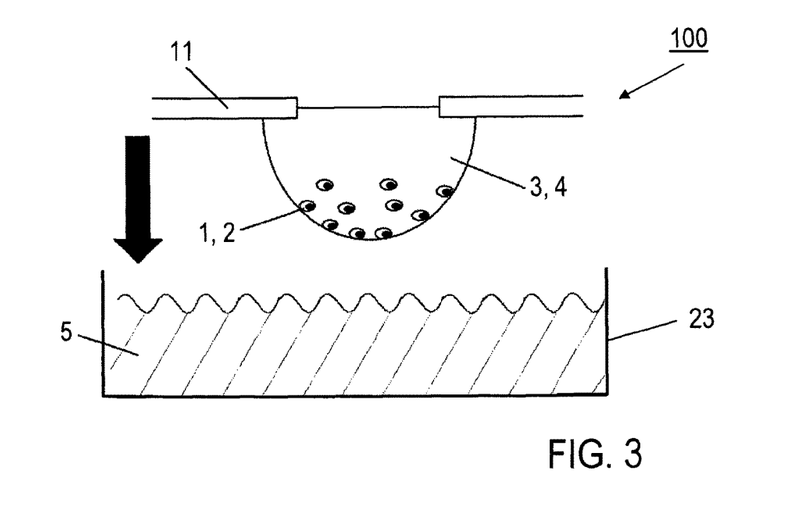
FIG. 3: a further variant of the polymerization of the hanging drop according to FIG. 1.

FIG. 3 shows a modified embodiment of the invention, in which the cross-linking device 20 comprises a bowl 23, in which the polymerization substance 5 is disposed as a fluid cross-linking means. In this case, the cross-linking of the hanging drop 3, having the sample 1 in the form of biological cells 2, is effected by reducing the distance between the holding device 11 and the bowl 23 until the hanging drop 3 is immersed in the polymerization substance 5. The inventors have found that, upon immersion, polymerization commences instantaneously on the surface of the hanging drop, such that its shape is maintained even during immersion in the polymerization substance 5.

Supplying of the polymerization to the hanging drop 3 causes the dissolved alginate to become cross-linked, such that a polymer capsule 4 is formed (FIG. 2). Following polymerization, the polymer capsule 4 continues to adhere to the holding device 11. For further use of the polymer capsule 4, the latter is mechanically and/or chemically separated from the holding device 11 (see below, FIGS. 8 to 10).

Figure 4:
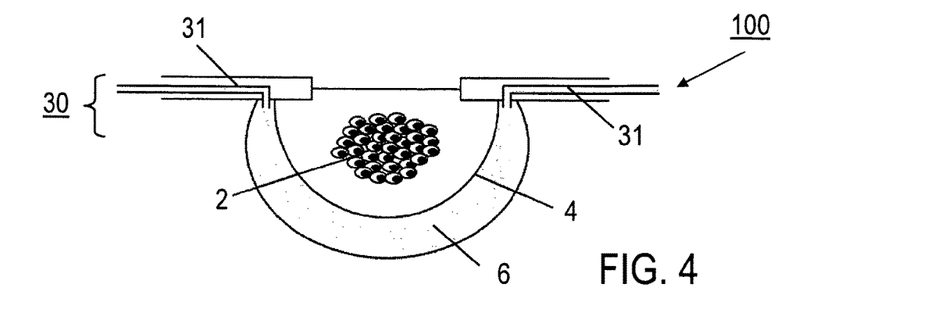
FIG. 4: the covering of a polymer capsule with a covering substance.

FIG. 4 shows an embodiment of the invention in which the encapsulation device 100 is provided with a covering device 30, comprising at least one fluid line 31 for supplying a covering substance 6 to the surface of the polymer capsule 4. In the example represented, two fluid lines 31 are fixedly connected to the holding device 11, and are disposed such that the fluid lines 31 open onto the surface of the polymer capsule 4. In modified variants of the invention, the covering device may be disposed separately from the holding device and comprise, for example, a third pipetting device.

The covering of the polymer capsule 4 with a covering substance may have various functions. For example, the surface of the polymer capsule 4 can be functionalized, for example additionally hardened or provided with additional chemical substances, or an additional polymer layer may be applied. The covering substance is preferably supplied in the fluid state and solidified on the surface of the polymer capsule 4. Alternatively, the covering substance may remain in the fluid state on the surface of the polymer capsule 4.

In the case of encapsulation of biological cells 2, the cultivation of the cells can be continued in the polymer capsule 4. In this case, the covering substance 6 preferably comprises a cultivation medium (nutrient and/or differentiation medium) that diffuses through the cross-linked alginate of the polymer capsule 4 to the cells 2.

Figure 5:
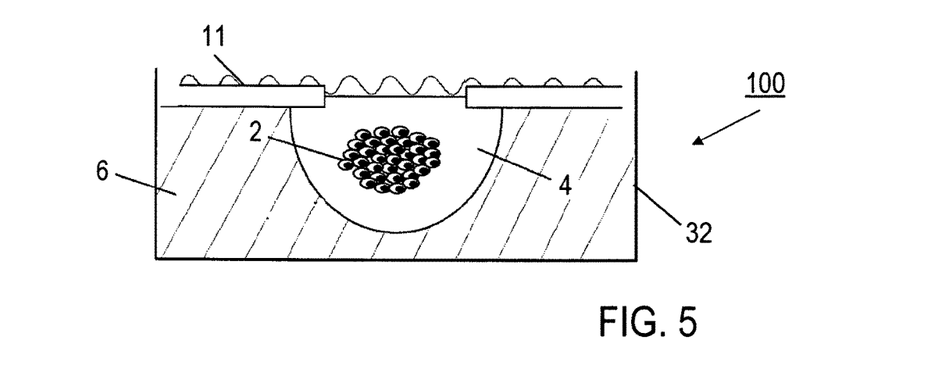
FIG. 5: cultivation of cells in a polymer capsule by means of a cultivation medium.

According to a further variant of the invention, the covering device may comprise a bowl 32 for receiving the covering substance 6, as shown schematically in FIG. 5. The covering substance 6 in the bowl 32 comprises, for example, a cultivation medium, which diffuses through the cross-linked alginate of the polymer capsule 4 to the cells 2. Preferably, the entire holding device 11 is immersed in the bowl 32, such that the polymer capsule 4 is wetted all over with the cultivation medium.

If the holding device 11 comprises a hole plate having a multiplicity of holes, for example a drop plate for cultivation in hanging drops, all polymer capsules 4 can be immersed simultaneously in a homogeneous cultivation medium, or they can be immersed selectively in each case, in differing cultivation media. For example, a multiplicity of bowls 32 may be provided, having a geometric arrangement corresponding to the geometric arrangement of the holes in the hole plate of the holding device 11, with like or differing cultivation media being disposed, as a covering substance 6, in the bowls 32. Advantageously, this variant of the invention can easily be realized with commercially available components such as, for example, a drop plate for the cultivation of cells in hanging drops and a matching microtiter plate for providing the bowls, for example in the "96-well format". In this case, each polymer capsule constitutes an alginate bioreactor having a differing composition of media, this being advantageously, in particular, for screening applications.

Figure 6:
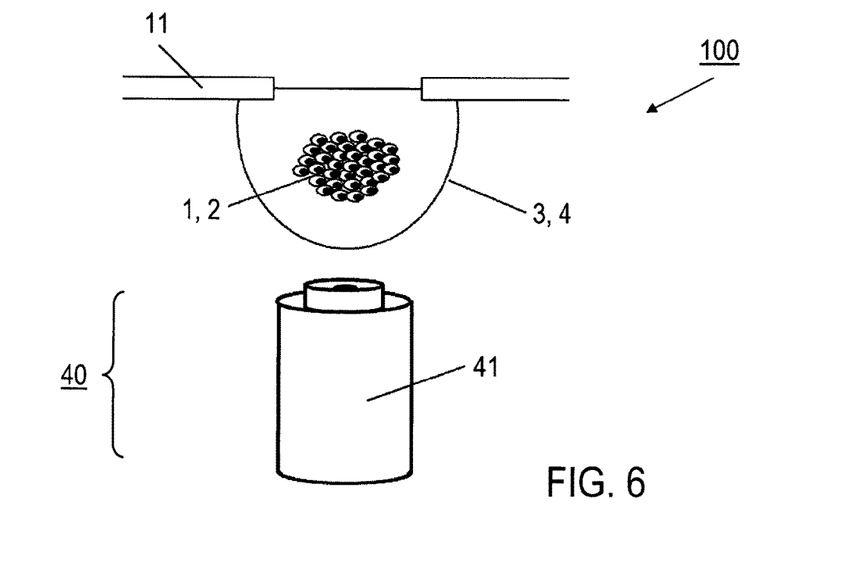
FIGS. 6 and 7: variants of optical or electrical measurements on the hanging drop.

It is shown schematically in FIG. 6 that, according to a further embodiment of the invention, the encapsulation device 100 may be provided with a measuring device 40. The measuring device 40 comprises, for example, a microscope 41 (represented in part) for optically capturing the state of the sample 1 in the hanging drop 3, or of the polymer capsule 4. The microscope 41 can be used, in particular, to monitor the further cultivation of cells 2 in the polymer capsule 4.

Figure 7:
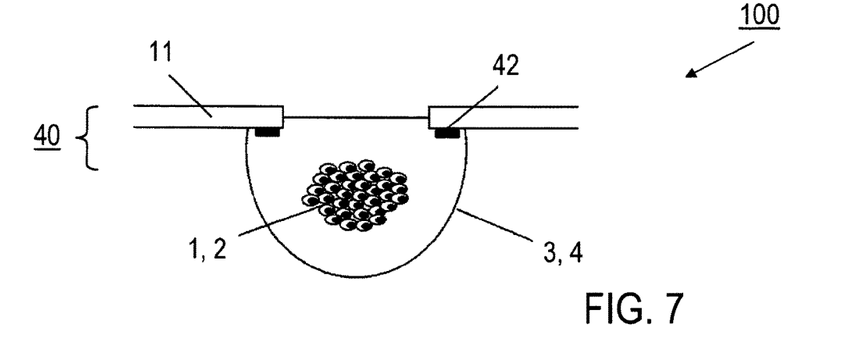

According to an alternative variant of the invention, which is shown in FIG. 7, the measuring device 40 may be used for electrical measurement on the hanging drop 3, or polymer capsule 4. In this case, the holding device 11 is provided with electrodes 42, which are disposed adjacently to the hole in the hole plate and connected to an impedance measuring device (not represented). Advantageously, the state of the sample 1 in the hanging drop 3, for example the number of cells 2, can be detected by means of an impedance measurement.

Figure 8:
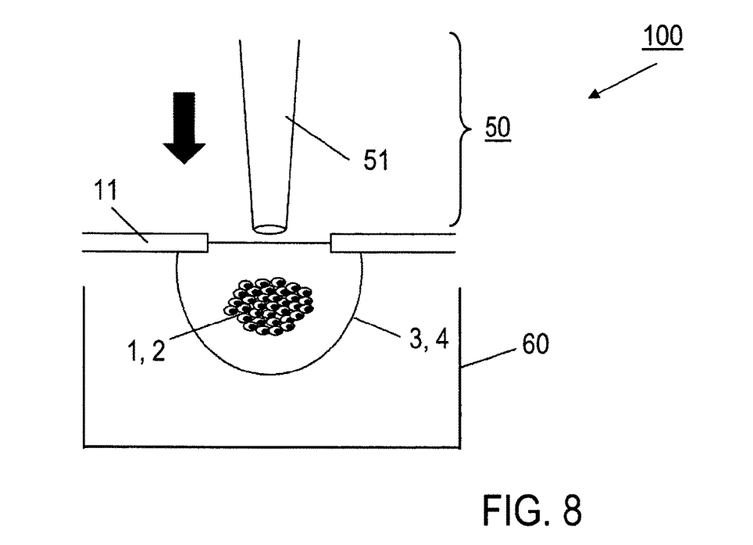
FIGS. 8 to 10: variants of separating of the polymerized drop from the holding device.
Figure 9:
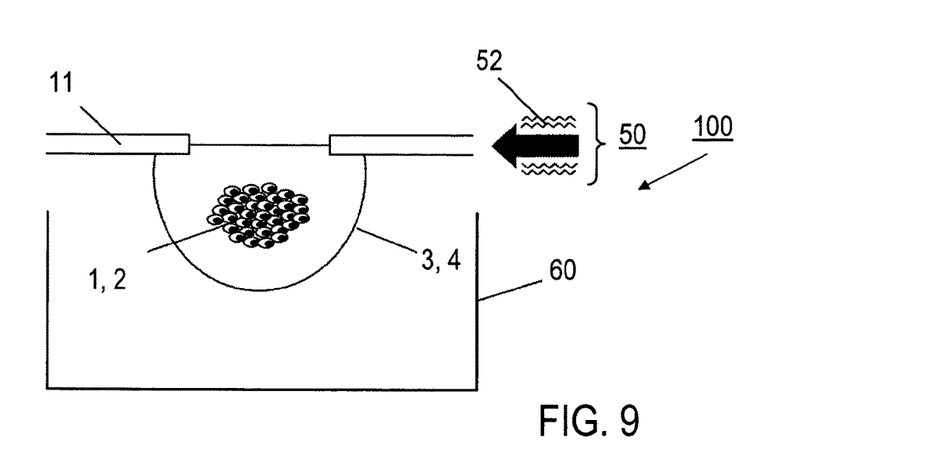
Figure 10:
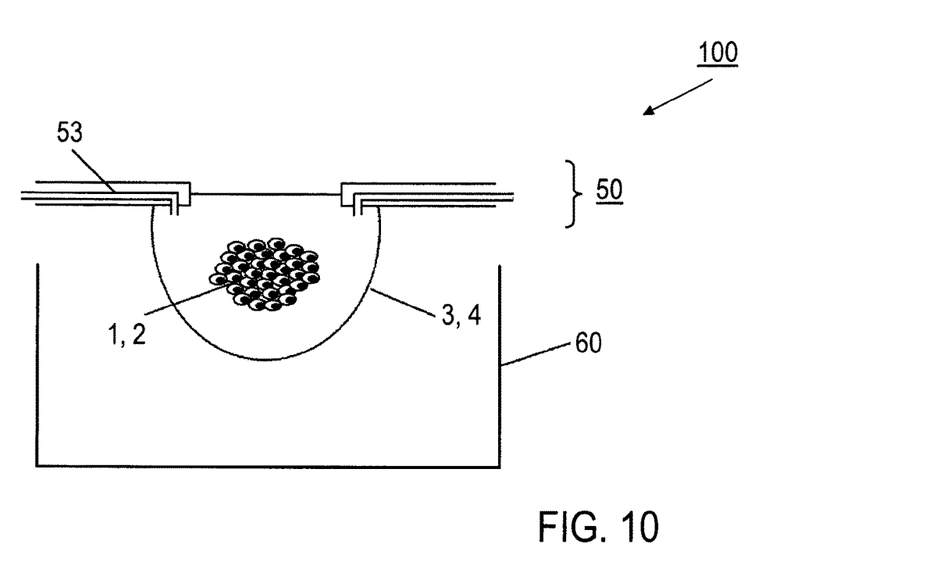

FIGS. 8 to 10 show different variants of the separating of the polymer capsules 4 from the holding device 11 by mechanical and/or chemical means. For the purpose of separation, the encapsulation device 100 is preferably provided with a separating device 50, which comprises, for example, a further pipetting device 51 (FIG. 8), an ultrasound generator 52 (FIG. 9), or fluid lines 53, which are connected to the holding device 11 (FIG. 10). According to FIG. 8, the polymer capsule 4 is moved into a collecting vessel 60 by a mechanical force exerted by means of the further pipetting device 51. The ultrasound generator 52 can be used to cause the holding device 11 to vibrate, in order to shake off the polymer capsule 4, such that it falls into the collecting vessel 60. Finally, a depolymerizing fluid such as, for example, EDTA, the action of which causes the polymer capsule 4 to be dissolved in the portions adjoining the holding device 11, such that it likewise falls into the collecting vessel 60, can be supplied via the fluid lines 53.

The encapsulation according to the invention may be applied, for example, in combination with the following process for the cultivation of biological cells. In a specific example, there is firstly a differentiation of hESCs or hiPSCs stem cells into cardiomyocytes, with a medicament cytotoxicity test (a so-called "embryonic stem cell test, EST") being performed subsequently.

Drops (20-40 μl) of a cell suspension of hESCs/hiPSCs are placed on the drop plate of the holding device 11 by means of a pipetting robot. Within three days, so-called embryoid bodies (EBs, spheroids) form from the cells. Microcarriers can then optionally be added to these multicellular aggregates, by means of the pipetting robot, such that the EBs adhere to the surfaces of the microcarriers.

In the next process step, the medium of the EBs, or of the EBs adhering to the microcarriers, is replaced by an alginate solution and cross-linked by means of the method according to the invention. The encapsulated EBs, attached to the drop plate, are then again fed with differentiation medium by means of micro-channels or by immersion of the complete drop plate.

Following differentiation of the cells into cardiomyocytes, identifiable by a rhythmic beating and twitching of the cell aggregates, screening of active substances for cytotoxic effects can be performed. In this case, the active substances can again be supplied through micro-channels, or by immersion of the plate in a multi-well plate having separate cavities, such that each drop is exposed separately to a concentration or composition of active substance.

Further examples for an application of the encapsulation according to the invention are optimization of the efficiency of differentiation of MSCs into osteoblasts, cultivation of functional chondrocytes, or production of encapsulated cells from hESCs/hiPSCs for immuno-isolated transplantation.

The features of the invention described in the above description, the drawings and the claims may be of importance, both singly and in combination, for the realization of the invention in its various designs.

The invention claimed is:

1. An encapsulation device, which is arranged to encapsulate a sample in a polymer capsule, comprising:
   a drop generator, which is arranged to provide a drop of a suspension that contains the sample, the drop generator comprising a holding device arranged to receive the drop of the suspension and hold the drop of the suspension in a hanging state to form a hanging suspension drop; and
   a cross-linking device arranged to supply a polymerization substance to the hanging suspension drop on the holding device and to form the polymer capsule.

2. The encapsulation device according to claim 1, in which the holding device comprises at least one of
   a holding plate having an exposed underside, which is arranged to receive the hanging drop,
   a hole plate, which has a hole for receiving the hanging drop,
   a mesh plate, which is arranged to receive the hanging drop, and
   a holding rod, which is arranged to receive the hanging drop.

3. The encapsulation device according to claim 1, in which
   the drop generator has a feed device, which is arranged to feed the suspension to the holding device and to form the hanging drop on the holding device.

4. The encapsulation device according to claim 3, in which
   the feed device comprises a first pipetting device, which is arranged to place the hanging drop on the holding device.

5. The encapsulation device according to claim 1, in which the cross-linking device comprises at least one of
   a particle shooting device, which is arranged to inject the polymerization substance into the hanging drop,
   a second pipetting device, which is arranged to introduce the polymerization substance into the hanging drop, and
   a bowl for receiving the polymerization substance, the holding device and the bowl being disposed so as to be movable relative to each other, such that the hanging drop can be immersed in the polymerization substance in the bowl.

6. The encapsulation device according to claim 1, in which
   a covering device is provided, which is arranged to cover the polymer capsule with a covering substance.

7. The encapsulation device according to claim 6, in which
   the covering device comprises at least one fluid line, which is fixedly connected to the holding device.

8. The encapsulation device according to claim 1, further comprising
   a measuring device, which is arranged to examine the hanging drop and/or the polymer capsule.

9. The encapsulation device according to claim 1, further comprising
   a separating device, which is arranged to separate the polymer capsule from the holding device.

10. A method for encapsulating a sample in a polymer capsule, comprising the steps:
    providing an encapsulation device according to claim 1,
    providing by use of the drop generator a drop of a suspension that contains the sample, and
    polymerizing the drop using the cross-linking device, wherein
    the drop is provided in a hanging state on the holding device, and
    the polymerizing comprises supplying of a polymerization substance to the hanging drop on the holding device and a polymerization reaction in the drop, such that the polymer capsule is formed.

11. The method according to claim 10, in which the providing of the hanging drop comprises at least one of
    receiving the hanging drop on an exposed underside of a holding plate,
    receiving the hanging drop in the holes of a hole plate,
    receiving the hanging drop on an exposed underside of a mesh plate, and
    receiving the hanging drop on a holding rod.

12. The method according to claim 10, in which
    the providing of the hanging drop comprises placing the hanging drop on the holding device by use of a first pipetting device.

13. The method according to claim 10, in which the polymerizing comprises at least one of
    introducing the polymerization substance into the hanging drop by use of a second pipetting device,
    injecting the polymerization substance into the hanging drop by use of a particle shooting device, and
    immersing the hanging drop in the polymerization substance in a bowl.

14. The method according to claim 10, further comprising at least one of the steps
    covering the polymer capsule with a covering substance, and
    examining the hanging drop or the polymer capsule.

15. The method according to claim 10, further comprising the step
    separating the polymer capsule from the holding device.

16. The method according to claim 10, in which
    the suspension contains an alginate solution, and the polymerization substance contains cross-linking ions by way of which the alginate solution is polymerized in the hanging drop, or
    the suspension contains cross-linking ions, and the polymerization contains an alginate solution, which is polymerized in the hanging drop.

17. The method according to claim 10, in which
    the sample contains at least one of at least one biological cell, at least one cell component and at least one cell group.

18. The encapsulation device according to claim 1, in which the holding device comprises
    a receptacle for the hanging suspension drop so that a top side of the hanging suspension drop can adhere to the holding device.

* * * * *